(12) United States Patent
Culley et al.

(10) Patent No.: US 7,682,526 B2
(45) Date of Patent: Mar. 23, 2010

(54) STABLE IMIDAZOLINE SOLUTIONS

(75) Inventors: Scott Anthony Culley, Midlothian, VA (US); José L. Reyes-Gavilan, Glen Allen, VA (US)

(73) Assignee: Afton Chemical Corporation, Richmond, VA (US)

( * ) Notice: Subject to any disclaimer, the term of this patent is extended or adjusted under 35 U.S.C. 154(b) by 631 days.

(21) Appl. No.: 11/315,794

(22) Filed: Dec. 22, 2005

(65) Prior Publication Data
US 2007/0145333 A1 Jun. 28, 2007

(51) Int. Cl.
C23F 11/00 (2006.01)
(52) U.S. Cl. .................. 252/387; 252/8.62; 252/392; 422/6; 422/16
(58) Field of Classification Search ............ 252/387, 252/392, 8.62; 422/6, 16
See application file for complete search history.

(56) References Cited

U.S. PATENT DOCUMENTS

| | | | |
|---|---|---|---|
| 2,160,273 A | 5/1939 | Loane et al. | |
| 2,384,577 A | 9/1945 | Thomas | |
| 2,621,195 A | 12/1952 | Haslam | |
| 2,710,872 A | 6/1955 | Thompson | |
| 2,719,125 A | 9/1955 | Roberts | |
| 2,719,126 A | 9/1955 | Fields et al. | |
| 2,786,866 A | 3/1957 | Hook et al. | |
| 2,897,152 A | 7/1959 | Elliott et al. | |
| 2,960,469 A | 11/1960 | Young | |
| 2,995,569 A | 8/1961 | Hamilton et al. | |
| 3,087,932 A | 4/1963 | Lille, Jr. | |
| 3,219,666 A | 11/1965 | Norman et al. | |
| 3,277,002 A | 10/1966 | Hunt et al. | |
| 3,356,702 A | 12/1967 | Farmer et al. | |
| 3,399,139 A | 8/1968 | Forbes et al. | |
| 3,407,222 A | 10/1968 | Lies | |
| 3,445,386 A * | 5/1969 | Logothetis et al. | 508/285 |
| 3,458,548 A | 7/1969 | Carlson | |
| 3,509,051 A | 4/1970 | Farmer et al. | |
| 3,565,804 A | 2/1971 | Honnen et al. | |
| 3,673,090 A | 6/1972 | Walbillig et al. | |
| 3,697,574 A | 10/1972 | Piasek et al. | |
| 3,699,118 A | 10/1972 | Donham | |
| 3,703,504 A | 11/1972 | Horodysky | |
| 3,703,505 A | 11/1972 | Horodysky et al. | |
| 3,736,357 A | 5/1973 | Piasek et al. | |
| 3,758,493 A | 9/1973 | Maddox, Jr. | |
| 3,762,890 A | 10/1973 | Collins | |
| 3,794,081 A | 2/1974 | Fiser et al. | |
| 3,796,661 A | 3/1974 | Suratwala et al. | |
| 3,821,236 A | 6/1974 | Ripple | |
| 3,867,359 A | 2/1975 | Beadle | |
| 3,873,454 A | 3/1975 | Horodysky et al. | |
| 3,904,537 A | 9/1975 | Ripple | |
| 3,969,281 A | 7/1976 | Sharp | |
| 4,029,587 A | 6/1977 | Koch | |
| 4,097,387 A | 6/1978 | Caspari | |
| 4,098,705 A | 7/1978 | Sakurai et al. | |
| 4,107,059 A | 8/1978 | King et al. | |
| 4,122,033 A | 10/1978 | Black | |
| 4,136,043 A | 1/1979 | Davis | |
| 4,164,473 A | 8/1979 | Coupland et al. | |
| 4,171,268 A | 10/1979 | Collins | |
| 4,176,073 A | 11/1979 | Ryer et al. | |
| 4,176,074 A | 11/1979 | Coupland et al. | |
| 4,178,258 A | 12/1979 | Papay et al. | |
| 4,188,299 A | 2/1980 | Caspari | |
| 4,192,757 A | 3/1980 | Brewster | |
| 4,193,882 A | 3/1980 | Gemmill, Jr. | |
| 4,210,683 A | 7/1980 | Praxl et al. | |
| 4,234,435 A | 11/1980 | Meinhardt et al. | |
| 4,248,720 A | 2/1981 | Coupland et al. | |
| 4,259,195 A | 3/1981 | King et al. | |
| 4,261,843 A | 4/1981 | King et al. | |
| 4,263,152 A | 4/1981 | King et al. | |
| 4,265,773 A | 5/1981 | De Vries et al. | |
| 4,266,945 A | 5/1981 | Karn | |
| 4,272,387 A | 6/1981 | King et al. | |
| 4,283,295 A | 8/1981 | De Vries et al. | |
| 4,285,822 A | 8/1981 | De Vries et al. | |
| 4,289,635 A | 9/1981 | Schroeck | |
| 4,362,633 A | 12/1982 | Spence et al. | |
| 4,363,322 A | 12/1982 | Andersson | |
| 4,369,119 A | 1/1983 | De vries et al. | |
| 4,383,931 A | 5/1983 | Ryu et al. | |
| 4,395,343 A | 7/1983 | De Vries et al. | |
| 4,402,840 A | 9/1983 | De Vries et al. | |
| 4,466,901 A | 8/1984 | Hunt et al. | |

(Continued)

FOREIGN PATENT DOCUMENTS

EP 330 522 12/1994

(Continued)

*Primary Examiner*—Ling-Siu Choi
*Assistant Examiner*—Bijan Ahvazi
(74) *Attorney, Agent, or Firm*—Luedeka, Neely & Graham, PC

(57) ABSTRACT

A imidazoline concentrate, uses of the concentrate, and methods of increasing a storage stability of solutions containing the concentrate are disclosed. The concentrate may include a reaction product of a fatty acid, an alkylene polyamine, a hydrocarbyl succinic acid or anhydride, and an alkoxylated alkylphenol component. The concentrate may contain from about 2 to about 50 wt. % of the alkyphenol component.

20 Claims, No Drawings

U.S. PATENT DOCUMENTS

| | | | |
|---|---|---|---|
| 4,479,883 A | 10/1984 | Shaub et al. | |
| 4,517,114 A | 5/1985 | Oppenlaender et al. | |
| 4,555,352 A | 11/1985 | Garner et al. | |
| 4,636,322 A | 1/1987 | Nalesnik | |
| 4,654,156 A | 3/1987 | Horodysky et al. | |
| 4,692,256 A | 9/1987 | Umemura et al. | |
| 4,702,850 A | 10/1987 | Gutierrez et al. | |
| 4,713,184 A * | 12/1987 | Zaid | 507/236 |
| 4,758,362 A | 7/1988 | Butke | |
| 4,765,918 A | 8/1988 | Love et al. | |
| 4,824,611 A | 4/1989 | Cells | |
| 4,837,190 A | 6/1989 | Summers, III et al. | |
| 4,838,931 A | 6/1989 | Liebl et al. | |
| 4,849,123 A | 7/1989 | Tipton et al. | |
| 4,857,214 A | 8/1989 | Papay et al. | |
| 4,867,890 A | 9/1989 | Colclough et al. | |
| 4,876,375 A | 10/1989 | Lam | |
| 4,885,365 A | 12/1989 | Lam | |
| 4,889,647 A | 12/1989 | Rowan et al. | |
| 4,904,401 A | 2/1990 | Ripple et al. | |
| 4,927,552 A | 5/1990 | Lam | |
| 4,938,880 A | 7/1990 | Waddoups et al. | |
| 4,957,643 A | 9/1990 | Lam | |
| 4,957,649 A | 9/1990 | Ripple et al. | |
| 4,962,256 A | 10/1990 | Le et al. | |
| 4,966,719 A | 10/1990 | Coyle et al. | |
| 4,978,464 A | 12/1990 | Coyle et al. | |
| 4,990,271 A | 2/1991 | Francis | |
| 4,995,996 A | 2/1991 | Coyle et al. | |
| 5,000,863 A | 3/1991 | Watanabe | |
| 5,027,901 A | 7/1991 | French et al. | |
| 5,055,211 A | 10/1991 | Habeeb et al. | |
| 5,055,521 A | 10/1991 | Parsy et al. | |
| 5,110,488 A | 5/1992 | Tipton et al. | |
| 5,137,647 A | 8/1992 | Karol | |
| 5,204,012 A | 4/1993 | Schaffhausen | |
| 5,242,613 A | 9/1993 | Ozablik et al. | |
| 5,260,466 A | 11/1993 | McGibbon | |
| 5,286,394 A | 2/1994 | Moore | |
| 5,287,731 A | 2/1994 | Florkowski et al. | |
| 5,292,480 A | 3/1994 | Fischer et al. | |
| 5,322,640 A | 6/1994 | Byrne et al. | |
| 5,328,620 A | 7/1994 | Ripple | |
| 5,401,661 A | 3/1995 | Florkowski et al. | |
| 5,412,130 A | 5/1995 | Karol | |
| 5,484,542 A | 1/1996 | Cahoon et al. | |
| 5,486,300 A | 1/1996 | Salomon et al. | |
| 5,490,945 A | 2/1996 | Smith et al. | |
| 5,562,864 A | 10/1996 | Salomon et al. | |
| 5,627,259 A | 5/1997 | Thaler et al. | |
| 5,633,326 A | 5/1997 | Patil et al. | |
| 5,643,859 A | 7/1997 | Gutierrez et al. | |
| 5,686,397 A | 11/1997 | Baranski et al. | |
| 5,693,598 A | 12/1997 | Abraham et al. | |
| 5,747,430 A | 5/1998 | Matsushita et al. | |
| 5,753,596 A | 5/1998 | Martin et al. | |
| 5,759,485 A | 6/1998 | Fischer et al. | |
| 5,773,391 A | 6/1998 | Lawate et al. | |
| 5,789,357 A | 8/1998 | Baranski et al. | |
| 5,792,729 A | 8/1998 | Harrison et al. | |
| 5,851,965 A | 12/1998 | Harrison et al. | |
| 5,853,434 A | 12/1998 | Harrison et al. | |
| 5,902,776 A | 5/1999 | Dohner et al. | |
| 5,936,041 A | 8/1999 | Diana et al. | |
| 5,939,362 A | 8/1999 | Johnson et al. | |
| 6,034,040 A | 3/2000 | Ozabalik et al. | |
| 6,074,444 A | 6/2000 | Bingley | |
| 6,096,691 A | 8/2000 | Conary et al. | |
| 6,103,674 A | 8/2000 | Nalesnik et al. | |
| 6,114,288 A | 9/2000 | Fujitsu et al. | |
| 6,117,826 A | 9/2000 | Baranski et al. | |
| 6,172,012 B1 | 1/2001 | Kumar et al. | |
| 6,232,276 B1 | 5/2001 | Stiefel et al. | |
| 6,300,291 B1 | 10/2001 | Hartley et al. | |
| 6,338,819 B1 * | 1/2002 | Braga et al. | 422/16 |
| 6,509,303 B1 | 1/2003 | Gatto | |
| 6,528,463 B1 | 3/2003 | Gatto et al. | |
| 6,599,472 B1 | 7/2003 | Hudson | |
| 6,599,865 B1 | 7/2003 | Esche, Jr. et al. | |
| 6,723,685 B2 | 4/2004 | Hartley et al. | |
| 6,797,677 B2 | 9/2004 | Esche, Jr. et al. | |
| 6,800,594 B2 * | 10/2004 | Miksic et al. | 507/240 |
| 2004/0200996 A1 | 10/2004 | Meyer | |
| 2004/0204325 A1 | 10/2004 | Takahashi | |
| 2004/0266630 A1 | 12/2004 | George et al. | |

FOREIGN PATENT DOCUMENTS

| | | |
|---|---|---|
| EP | 874040 | 10/1998 |
| EP | 0995790 | 4/2000 |
| GB | 885679 | 12/1961 |
| GB | 997335 | 7/1965 |
| GB | 1560830 | 2/1980 |
| GB | 866054 | 4/1991 |
| JP | 62236894 | 10/1987 |
| JP | 2004149762 | 5/2004 |
| WO | WO 8704454 | 7/1987 |
| WO | WO 9811181 | 3/1998 |
| WO | WO 02092734 | 11/2002 |

* cited by examiner

STABLE IMIDAZOLINE SOLUTIONS

TECHNICAL FIELD

The embodiments described herein relate to imidazoline compositions and in particular to additive solutions containing imidazoline compositions that remain stable under extremely low temperature applications.

BACKGROUND AND SUMMARY

Imidazolines may be used as corrosion inhibitors and/or rust inhibitors in a variety of applications including refinery operations, oil and gas well drilling fluids and pipelines therefor, and in storage containers for petroleum products. Other uses of imidazolines include, but are not limited to, biocides, herbicides, pesticides, and as additives for metal working fluids. Imidazoline compositions are typically provided as concentrates dissolved in solvents to allow delivery of a desired amount to a fluid. If imidazoline solutions are stored in a location where ambient temperatures drop below 0° C., the solutions may freeze, separate, or form sediment thus inhibiting the delivery of sufficient imidazoline to the desired fluid.

Alcohol-water imidazoline solutions are relatively low cost, have relatively low freezing points and are good solvents in locations that experience moderately low temperatures. However, alcohol-water solutions of imidazolines can separate, solidify, or otherwise become inhomogeneous at extremely low temperatures such as found in arctic locations. Accordingly, there is a need for imidazoline solutions that remain stable and clear at temperatures below about –20° C.

With regard to the foregoing, one or more embodiments described herein may provide an imidazoline concentrate, uses of the concentrate and methods of increasing a storage stability of the concentrate. The concentrate includes a reaction product of a fatty acid, an alkylene polyamine, a hydrocarbyl succinic acid or anhydride, and an alkoxylated alkylphenol component. The concentrate contains from about 2 to about 50 wt. % of the alkyphenol component.

In other embodiments, there are provided pipeline additives, oil well additives, and refinery additives. Each additive includes a reaction product of a fatty acid, an alkylene polyamine, a hydrocarbyl succinic acid or anhydride, and an alkoxylated alkylphenol component. The additive contains from about 2 to about 50 wt. % of the alkyphenol component.

In yet another embodiment there is provided a method for increasing a storage stability of an imidazoline concentrate. According to the method, from about 50 to about 95 wt. % of an imidazoline derived from a fatty acid, an alkylene polyamine, and a hydrocarbyl succinic acid or anhydride is blended with from about 2 to about 50 wt. % of an alkoxylated alkylphenol component.

The compositions and methods described herein are particularly suitable for additive solutions that may be used in extremely cold environments, such as in arctic regions. In addition to a greater storage stability of the additive solutions containing the imidazoline concentrates described herein, the imidazoline concentrates also may exhibit low flash points and low volatility. Other features and advantages of the compositions and methods described herein may be evident by reference to the following detailed description which is intended to exemplify aspects of the embodiments without intending to limit the embodiments described herein.

It is to be understood that both the foregoing general description and the following detailed description are exemplary and explanatory only and are intended to provide further explanation of the embodiments disclosed and claimed.

DETAILED DESCRIPTION OF EXEMPLARY EMBODIMENTS

In one embodiment is presented a relatively stable imidazoline additive solution. The terms "stable," "stability," "stabilized," and the like are intended to describe a property of the additive solution wherein the imidazoline component remains dissolved or solublized in a solvent over a prolonged period of time.

The terms "soluble" and "solubilized" mean that the imidazoline concentrate is substantially dissolved in a solvent so that an additive solution containing the imidazoline remains substantially clear of solids, precipitates, emulsions and the like.

As used herein, "hydrocarbon" means any of a vast number of compounds containing carbon, hydrogen, and/or oxygen in various combinations.

The term "hydrocarbyl" refers to a group having a carbon atom attached to the remainder of the molecule and having predominantly hydrocarbon character. Examples of hydrocarbyl groups include:

(1) hydrocarbon substituents, that is, aliphatic (e.g., alkyl or alkenyl), alicyclic (e.g., cycloalkyl, cycloalkenyl) substituents, and aromatic-, aliphatic-, and alicyclic-substituted aromatic substituents, as well as cyclic substituents wherein the ring is completed through another portion of the molecule (e.g., two substituents together form an alicyclic radical);

(2) substituted hydrocarbon substituents, that is, substituents containing non-hydrocarbon groups which, in the context of the description herein, do not alter the predominantly hydrocarbon substituent (e.g., halo (especially chloro and fluoro), hydroxy, alkoxy, mercapto, alkylmercapto, nitro, nitroso, and sulfoxy);

(3) hetero-substituents, that is, substituents which, while having a predominantly hydrocarbon character, in the context of this description, contain other than carbon in a ring or chain otherwise composed of carbon atoms. Hetero-atoms include sulfur, oxygen, nitrogen, and encompass substituents such as pyridyl, furyl, thienyl and imidazolyl. In general, no more than two, preferably no more than one, non-hydrocarbon substituent will be present for every ten carbon atoms in the hydrocarbyl group; typically, there will be no non-hydrocarbon substituents in the hydrocarbyl group.

Imidazoline Component

According to embodiments of the disclosure, a major component of the concentrates described herein is an imidazoline. Imidazolines are nitrogen containing heterocyclic compounds obtained by the reaction of a carboxylic acid with a polyamine at elevated temperatures. The imidazolines may be substituted with a variety of alkyl chains. In addition, the imidazolines can be further reacted with acids (organic and inorganic), anhydrides, alkyl halides, and numerous reactive species to form derivatives that have desirable properties. Accordingly, without limitation thereof, a suitable imidazoline that is useful as a corrosion inhibitor is a composition of the formula:

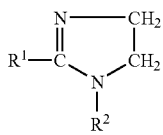

wherein $R^1$ selected from the group consisting of hydrogen and a hydrocarbyl group containing from about 1 to about 29 carbon atoms, and $R^2$ comprises a hydrocarbyl succinic acid or anhydride having from about 6 to about 100 carbon atoms in the hydrocarbyl group. An imidazoline of the foregoing formula may be made by reacting a fatty acid, an alkylene polyamine, and an excess of hydrocarbyl succinic acid or anhydride as generally described in U.S. Pat. No. 3,445,386.

As set forth above, imidazolines may be used as corrosion inhibitors, herbicides, pesticides, biocides, surfactants, emulsifiers and the like. For example, imidazolines have been used as corrosion inhibitors in automotive lubricants, hydraulic fluids, industrial lubricants, and metal working fluids to name a few. Imidazolines are also widely used in oil and gas field applications as well as in petroleum pipelines and storage containers as corrosion inhibitors since oil, brine, water, and impurities in the oil recovery process are highly corrosive to iron and steel alloys. In the foregoing applications, concentrates containing the imidazolines may be formulated with other components such as biocides, friction reducers, antifoams, scale inhibitors, hydrogen sulfide and oxygen scavengers, emulsion breakers, emulsifiers, antioxidants, and the like. Accordingly, the amount of imidazoline in a fluid that is effective to provide corrosion inhibition may range from about 5 to about 500 ppm, with a range of from about 10 to about 20 ppm of the imidazoline being typically used.

Certain imidazolines, particularly organic acids that have been neutralized with imidazolines, may be used as corrosion inhibitors for pipelines and oil wells. Imidazolines may be used in organic solvents for oil based drilling fluids or for pipeline applications that employ oil in water or water in oil emulsions of crude oil. Imidazolines may also be used in water or alcohol/water mixtures for water based drilling fluids. Imidazolines that are formulated into aqueous emulsions may be effective to control oil well corrosion for longer times than other systems.

Since imidazolines are highly viscous they are usually prepared as solutions in oil, water-alcohol mixtures, or organic solvents in concentrations of about 10-50 wt. %. The solvents used for the imidazolines may also be known as carrier fluids in the literature. In embodiments described in this disclosure, imidazoline solutions may be referred to as "additive solutions" since they may also contain other additives and components suitable for a particular application.

Due to their relatively high viscosity, imidazolines are typically used as a dilute solution of the imidazoline. Thus, the imidazoline concentrates are often dispersed or dissolved in alcohol-water mixtures, aqueous emulsions, or organic solvents so that the imidazoline concentrates may be pumped into oil wells, pipelines and the like in a predetermined amount. In some applications, alcohol-water mixtures are desirable because of their relatively low cost and provide additive solutions with relatively low freezing points. Many of the foregoing imidazoline solutions may be clear and homogenous at moderate temperatures however, at some point below 0° C., the imidazoline solutions may become hazy, inhomogeneous, separate, freeze, or deposit sediment. If storage conditions are such that an imidazoline solution cannot be kept at a minimum temperature when ambient temperatures decrease, then the solution may become unsuitable for use.

Surfactant

In order to provide stable imidazoline solutions suitable for long term storage in extremely cold climates, a suitable non-ionic surfactant is incorporated into the imidazoline concentrate. The imidazoline concentrate may be dissolved in the non-ionic surfactant, or the non-ionic surfactant may be added as a separate component to the imidazoline concentrate. The surfactant is desirably selected to provide an imidazoline solution that remains substantially clear, relatively fluid, and essentially homogeneous down to about –45° C. or lower for extended periods of time.

A suitable surfactant is advantageously a non-ionic surfactant selected from the group consisting of alkylphenol alkoxylate surfactants having an average of from about 3 to about 20 alkoxy groups per molecule. The alkyl moiety of the alkyphenol may contain from about 6 to about 25 carbon atoms therein and desirably contains from about 6 to about 10 carbon atoms. Useful non-ionic surfactants include, but are not limited to ethyoxylated nonylphenol surfactants containing from about four to about nine ethoxy groups per molecule. Such ethoxylated nonylphenol surfactants have an HLB of about 13.

In the imidazoline concentrates described herein, the surfactant is generally employed in an amount of from about 2 to about 50% by weight based on the total weight of imidazoline and surfactant. Suitable compositions may contain from about 5 to about 50 wt. % surfactant and from about 25 to about 95 wt. % of the imidazoline component.

Concentrates containing the imidazoline and surfactant may be used, for example, to provide corrosion inhibitors for petroleum pipelines and in oil well equipment. In such applications, the concentrates may include pipeline additives and alcohol/water mixtures to further enhance the low temperature capabilities of the corrosion inhibitor concentrate. Suitable alcohols include, but are not limited to, alcohols containing from about 1 to about 10 carbon atoms. When used, the alcohol may be present in the additive solution in an amount ranging from about 1 to about 50 wt. % of the total weight of the solution including the imidazoline and surfactant. Typically, such solutions may contain up to about 30 wt. % alcohol. Additive solutions containing the imidazoline, alcohol, water, and surfactant may be used wherein the imidazoline is present in the additive solution in an amount ranging from about 10 to about 30 percent by weight based on the total weight of the solution.

Other Components

The additive solutions described herein may also include other components for use in particular applications. For example, biocides such as quarternary ammonium chloride may be used. Examples of biocides include alkyl or dialkyl dimethyl benzyl ammonium chloride having an alkyl or dialkyl group varying from $C_8$ to $C_{20}$. Specific examples include, but are not limited to, didecyl dimethyl ammonium chloride, octyl decyl dimethyl ammonium chloride, and dioctyl dimethyl ammonium chloride.

Friction reducers that may be used with the additive solutions described herein may include, but are not limited to, homopolymers of acrylic acid, methacrylic acid or maleic anhydride and copolymers containing acrylic acid or methacrylic acid, which copolymers also contain at least one of the monomers chosen from the group consisting of acrylamide, methacrylamide, maleic anhydride, hydroxypropylacrylates, hydroxyethylacrylates, N-tertiary butyl acrylamide, 2-acrylamido-2-methylpropane sulfonate, sulfomethyl acrylamide, sulfomethyl methacrylamide, sulfoethylacrylamide, sulfonated styrene, vinyl sulfonate, itaconic acid, or N-hydroxypropylacrylamide. Useful dispersion polymers may be obtained commercially from the Hymo Corporation of Tokyo, Japan. Cationic water-soluble polymers may be synthesized from monomers of methacrylate, acrylate, or methacrylamide quaternary salts, or diallyldimethylammonium chloride as homopolymers or as co-polymers with acrylamide. Non-ionic water soluble polymers may be homopolymers of acrylamide or co-polymers of acrylamide and other suitable monomers.

Foam control may be provided by many compounds including, but not limited to, an antifoamant of the polysiloxane type, for example, silicone oil or polydimethyl siloxane.

Scale inhibitors that may be used with the additive solutions described herein, include, but are not limited to, alkali metal phosphates, alkali metal tripolyphosphates, alkali pyrophosphates, and organophosphonic acid scale inhibitors. A suitable organophosphonic scale inhibitor includes aminotris (methylene phosphonic acid). Another suitable scale inhibitor includes hydroxyethylidene phosphonic acid.

Suitable sulfur or sulfide scavengers for use in the additive solutions described herein include, without limitation, any compound capable of reacting with hydrogen sulfide, mercaptans, alkyl, di, and polysulfides and converting them to more benign sulfur-containing compounds. Other sulfur scavengers include amines, reaction products of aldehydes or aldehyde donors, and amines or amine donors such as imines, triazines, amine-aldehyde polymers, etc., or any other compound capable of reaction with noxious sulfur-containing species such as hydrogen sulfide, thiols, etc. or mixtures or combinations thereof.

Suitable oxygen scavengers include, but are not limited to, erythorbates, ascorbates, diethylhydroxyamine, or other oxygen reactive compounds such as potassium (alkali) salts of esters of glycols, polyhydric alcohol ethyloxylates or other similar compounds. Other exemplary oxygen scavengers include mixtures of tetramethylene diamines, hexamethylene diamines, 1,2-diaminecyclohexane, amine heads, or reaction products of such amines with partial molar equivalents of aldehydes. Still other oxygen control agents include salicylic and benzoic amides of polyamines, used especially in alkaline conditions, short chain acetylene diols or similar compounds, phosphate esters, borate glycerols, urea and thiourea salts of bisoxalidines or other compound that either absorb oxygen, react with oxygen or otherwise reduce or eliminate oxygen.

A small amount of a demulsifying component may be used. A preferred demulsifying component is described in EP Pat. No. 330,522, the disclosure of which is herein incorporated by reference. Such demulsifying component may be obtained by reacting an alkylene oxide with an adduct obtained by reacting a bis-epoxide with a polyhydric alcohol.

Emulsifiers that may be used with the additive solutions described herein, include but are not limited to, alkoxylated amines, glycols, alcohols, and phenols.

Another component of the additives solutions described herein is a dimerized unsaturated fatty acid. Suitable dimerized unsaturated fatty acids include dimers of comparatively long chain fatty acid, e.g. containing from about 8 to about 30 carbon atoms. The dimer acid may be substantially pure dimer acid or may be a material sold commercially and known as "dimer acid". Such commercially available material may be prepared by dimerizing unsaturated fatty acid and consists of a mixture of monomer, dimmer, and trimer of the acid. A particularly useful dimer acid is the dimer of linoleic acid.

Still another component of the additive solutions described herein includes phosphorus acid esters. Such components include esters of phosphorus acid, such as phenyl, benzl, cresyl, or xylyl phosphates and phosphites. Similarly, higher homologous aryl, alkaryl, or aralkyl phosphates and phosphites may be used. Such esters may be obtained according to known methods which involve reacting an alcohol with phosphorus pentoxide or $POCl_3$ to form the phosphates and by reacting the appropriate alcohol with phosphorus trichloride to form the phosphites. Specific examples of phosphorus acid esters include tricresyl phosphate, tricresyl phosphite, phenyl dicresyl phosphate, and the like. A particularly suitable phosphorus acid ester is diamyl phenyl hydrogen phosphate. Other phosphorus acid esters which may be used include the organic dialkyl phosphonates having hydrogen bonded to phosphorus. Representative of these compounds are: di-n-butyl phosphonate, diisopropyl phosphonate, dioctyl phosphonate, bis (2-ethylhexyl) phosphonate, di-sec-butyl phosphonate, diisobutyl phosphonate, di-tert-butyl phosphonate, bis(1,3-dimethylbutyl) phosphonate, diamyl phosphonate, bis(2-chloro 1-methylethyl) phosphonate, ditolyl phosphonate, diethyl phosphonate, bis(.beta.-chloroisopropyl phosphonate, O,S-dimethyl thiophosphonate, diphenyl phosphonate, ditolyl thiophosphonate, (tolyl) (isooctenyl) phosphonate, ditolyl phosphonate, dimethyl phosphonate, and methyl tolyl phosphonate.

Antioxidants may also be used in the additives solutions described herein. Such antioxidants include hindered phenols, sulfurized hindered phenols, alkaline earth metal salts of alkylphenolthioesters having $C_5$ to $C_{12}$ alkyl side chains, sulfurized alkylphenols, metal salts of either sulfurized or non-sulfurized alkylphenols, for example calcium nonylphenol sulfide, ashless oil soluble phenates and sulfurized phenates. Other antioxidants that may be used include sterically hindered phenols. Non-limiting examples of sterically hindered phenols include, but are not limited to, 2,6-di-tertiary butylphenol, 2,6 di-tertiary butyl methylphenol, 4-ethyl-2,6-di-tertiary butylphenol, 4-propyl-2,6-di-tertiary butylphenol, 4-butyl-2,6-di-tertiary butylphenol, 4-pentyl-2,6-di-tertiary butylphenol, 4-hexyl-2,6-di-tertiary butylphenol, 4-heptyl-2,6-di-tertiary butylphenol, 4-(2-ethylhexyl)-2,6-di-tertiary butylphenol, 4-octyl-2,6-di-tertiary butylphenol, 4-nonyl-2,6-di-tertiary butylphenol, 4-decyl-2,6-di-tertiary butylphenol, 4-undecyl-2,6-di-tertiary butylphenol, 4-dodecyl-2,6-di-tertiary butylphenol, methylene bridged sterically hindered phenols including but not limited to 4,4-methylenebis(6-tert-butyl-o-cresol), 4,4-methylenebis(2-tert-amyl-o-cresol), 2,2-methylenebis(4-methyl-6 tert-butylphenol, 4,4-methylenebis(2,6-di-tert-butylphenol) and mixtures thereof as described in U.S. Publication No. 2004/0266630.

Additive solutions containing the components described above may be provided generally in accordance with the amounts of each of the components listed in the following table:

| Component | Concentration Range in Wt. % |
| --- | --- |
| Imidazoline | 10-30 |
| Non-ionic surfactant | 1-20 |
| Alcohol | 5-40 |
| Water | 5-40 |
| Dimer acid | 0-20 |

-continued

| Component | Concentration Range in Wt. % |
|---|---|
| Phosphate | 0-5 |
| Dodecyl succinic acid | 1-15 |
| Other additive components | 1-30 |

The following non-limiting examples of imidazoline solutions are provided for the purpose of illustrating aspects of the exemplary embodiments. The imidazoline provided for use in the examples was a reaction product of oleic acid and triethylene tetramine. The reaction product was further reacted with an excess of hydrocarybl substituted succinic anhydride. The resulting product was blended with a dimer acid, a di-t-amylphenyl hydrogen phosphate, and a polyether to make an imidazole concentrate containing 100 wt. % of the active imidazoline product.

Each of the samples was placed in a freezer to simulate temperatures that are found in arctic locations where oil is drilled and piped during the winter. The concentrations of the imidazoline product in the final solutions were 15 wt. % except for Comparative Example 2 where the imiadazoline product in the final solution was 30 wt. %.

COMPARATIVE EXAMPLE 1

An imidazoline product as described above was dissolved in a 50:50% by weight mixture of methanol and water at 15 wt. % along with a pipeline additive package consisting of friction reducers and other components at 26 wt. %. The clear amber solution was placed in a −45° C. freezer overnight. Upon examination the next day the solution was hazy and opaque.

COMPARATIVE EXAMPLE 2

An imidazoline product as described above was dissolved in a 50:50% by weight mixture of methanol and water at 30 wt. % along with a pipeline additive package consisting of friction reducers and other components at 26 wt. %. The clear amber solution was placed in a −45° C. freezer overnight. Upon examination the next day the solution was viscous, hazy and opaque.

COMPARATIVE EXAMPLE 3

The imidazoline product of Comparative Example 1 was solubilized in ethylene glycol n-butyl ether at 50 wt. %. The solubilized imidazoline was dissolved in a 50:50% by weight mixture of methanol and water mixture at 30 wt. % along with a pipeline additive package consisting of friction reducers and other components at 26 wt. %. The clear amber solution was placed in a −45° C. freezer overnight. Upon examination the next day the solution was hazy and opaque.

COMPARATIVE EXAMPLE 4

The imidazoline product of Comparative Example 1 was solubilized in ethylene glycol n-butyl ether at 50 wt. %. The solubilized imidazoline was dissolved in a methanol at 30 wt. % along with a pipeline additive package consisting of friction reducers and other components at 26 wt. %. The clear amber solution was placed in a −45° C. freezer overnight. Upon examination the next day the solution was hazy. The solution was placed back in the freezer for six weeks and at which time it was examined and found to have a sediment layer on the bottom.

The following examples 5 and 6 illustrate embodiments of the disclosure described herein.

EXAMPLE 5

The imidazoline product of Comparative Example 1 was solubilized at 50 wt. % in a non-ionic ethoxylated nonophenol containing about 9 ethoxy groups per molecule. The solubilized imidazoline was dissolved in a 50:50% by weight mixture of methanol and water at 30 wt. % along with a pipeline additive package consisting of friction reducers and other components at 26 wt. %. The clear amber solution was placed in a −45° C. freezer overnight. Upon examination the next day the solution was clear and remained fluid. The solution was placed back in the freezer for six weeks at which time it was examined and found to be clear and fluid. Upon warming to room temperature the solution remained clear, fluid, and homogeneous.

EXAMPLE 6

The imidazoline product of Comparative Example 1 was solubilized in a non-ionic ethoxylated nonophenol containing about 9 ethoxy groups per molecule at 85 wt. %. The solubilized imidazoline was dissolved in a 50:50% by weight mixture of methanol and water at 17.65 wt. % along with pipeline additive package consisting of friction reducers and other components at 26 wt. %. The clear amber solution was placed in a −45° C. freezer overnight. Upon examination the next day the solution was clear and fluid.

Comparative Example 1 showed that when the imidazoline product was dissolved in the methanol-water mixture at 15 wt. % and placed in the freezer the solution became hazy at low temperatures and formed an opaque solution. Because of the haziness of the solution, it is not possible to ascertain whether the solution would be homogeneous and free of sediment in the field.

Comparative Example 2 showed the effect of solubilizing the imidazoline product at 30 wt. % in the methanol-water mixture. The outcome was substantially the same as in Comparative Example 1.

Comparative Example 3 showed the effect of solubilizing the imidazoline product in an organic solvent to make a solubilized imidazoline before dissolving the solubilized imidazoline in the methanol-water mixture. The outcome was substantially the same as Comparative Example 1.

Example 4 showed the effect of dissolving the solubilized imidazoline of Comparative Example 3 in methanol without water. In this example the solution became unstable and formed solids which settled on the bottom. Such a solution is undesirable since the sediment would detract from the active components in the mixture. Moreover, the solids could plug lines and equipment used to pump the solution into the pipeline or oil well.

Examples 5 and 6 showed the beneficial effect of solubilizing the imidazoline with an alkoxylated alkylphenol to make a solubilized imidazoline containing a surfactant before dissolving the solution into methanol-water mixture. In these examples the additive solutions remained clear and fluid without the formation of sediment or flocculant. Examples 5 and 6 illustrated the ability of the alkoxylated alkylphenol to provide stable imidazoline solutions at extremely low temperatures.

As shown by Examples 5 and 6, the imidazoline/surfactant solution is stable indefinitely. Furthermore it was shown by Examples 1-4 that neat imidazolines, imidazoline emulsions, or imidazoline concentrates based on organic solvents are not stable in alcohol-water mixtures at extremely low temperatures in the absence of the surfactant.

Similar tests for stability were conducted with the imidazoline and surfactant mixtures in methanol/water mixtures at −45° C. at concentrations of the imidazoline product ranging from about 10 wt. % to about 16 wt. %. Such mixtures also provided stable solutions.

It is expected that alkoxylated alkylphenols having from about 4 to about 15 alkoxy groups per molecule are suitable for providing stable solutions of imidazoline in alcohol/water mixtures. While the foregoing examples used methanol, other alcohols such as ethanol, butanol, glycol, etc. may be used to provide a suitable solvent for the imidazoline solution. Moreover, the ratio of alcohol to water may be widely varied to suit the particular application.

At numerous places throughout this specification, reference has been made to a number of U.S. patents and publications. All such cited documents are expressly incorporated in full into this disclosure as if fully set forth herein.

The foregoing embodiments are susceptible to considerable variation in its practice. Accordingly, the embodiments are not intended to be limited to the specific exemplifications set forth hereinabove. Rather, the foregoing embodiments are within the spirit and scope of the appended claims, including the equivalents thereof available as a matter of law.

The patentees do not intend to dedicate any disclosed embodiments to the public, and to the extent any disclosed modifications or alterations may not literally fall within the scope of the claims, they are considered to be part hereof under the doctrine of equivalents.

What is claimed is:

1. A concentrate for use in providing an additive solution suitable for a pipeline fluid, a refinery fluid, an oil and gas well drilling fluid, or a petroleum product consisting essentially of
    a) a reaction product of an imidazoline, and a hydrocarbyl succinic acid or anhydride;
    b) an alkoxylated alkylphenol component; and,
    c) optionally, one or more of a dimer acid, a phosphate, and a polyether,
    wherein the concentrate contains from about 2 to about 50 wt. % of the alkyphenol component and the concentrate remains stable and substantially clear down to about −45° C. in the presence of alcohol, water in an amount ranging from about 5 to about 40 percent by weight based on the total weight of the concentrate, friction reducers, and other components.

2. The concentrate of claim 1, further consisting essentially of a dimer acid, a phosphate and a polyether.

3. The concentrate of claim 1, wherein the imidazoline is derived from oleic acid and triethylene tetramine and wherein the hydrocarbyl succinic acid or anhydride comprises dodecyl succinic acid or anhydride.

4. The concentrate of claim 1, wherein the alkylphenol component comprises an ethoxylated alkylphenol component.

5. The concentrate of claim 4, wherein the alkyphenol component comprises from about 4 to about 15 ethoxy groups.

6. The concentrate of claim 5, wherein the alkylphenol component comprises nonylphenol.

7. An additive solution comprising (a) the concentrate of claim 1, (b) a mixture of alcohol and water, (c) friction reducers, and (d) other components.

8. A pipeline fluid comprising the additive solution of claim 7 in an amount effective to reduce corrosion of a pipeline in contact with the pipeline fluid.

9. A refinery fluid stream comprising the additive solution of claim 7 in an amount effective to reduce corrosion of equipment and pipelines in contact with the fluid stream.

10. An oil and gas well drilling fluid comprising the additive solution of claim 7 in an amount effective to reduce corrosion of equipment and pipelines in contact with the drilling fluid.

11. A petroleum product comprising the additive solution of claim 7 in an amount effective to reduce corrosion of a container in contact with the petroleum product.

12. The additive solution of claim 7, further comprising a scale inhibitor.

13. A method of increasing a storage stability of a concentrate for use in providing an additive solution suitable for a pipeline fluid, a refinery fluid, an oil and gas well drilling fluid, or a petroleum product consisting essentially of blending (a) a reaction product of imidazoline and a hydrocarbyl succinic acid or anhydride with (b) from about 2 to about 50 wt. % of an alkoxylated alkylphenol component; and (c) optionally, one or more of a dimer acid, a phosphate, and a polyether, wherein the concentrate remains stable and substantially clear down to about −45° C. in the presence of alcohol, water in an amount ranging from about 5 to about 40 percent by weight based on the total weight of the concentrate, friction reducers, and other components.

14. The method of claim 13, wherein the additive solution comprising the concentrate comprises a mixture of alcohol and water, friction reducers, and other components.

15. The method of claim 14, wherein the additive solution further comprises a scale inhibitor.

16. The method of claim 13, wherein the concentrate includes a dimer acid, a phosphate and a polyether.

17. The method of claim 13, wherein the imidazoline is derived from oleic acid and triethylene tetramine and wherein the hydrocarbyl succinic acid or anhydride comprises dodecyl succinic acid or anhydride.

18. The method of claim 13, wherein the alkylphenol component comprises an ethoxylated alkylphenol component.

19. The method of claim 18, wherein the alkylphenol component comprises from about 4 to about 15 ethoxy groups.

20. The method of claim 19, wherein the alkylphenol component comprises nonylphenol.

* * * * *